(12) United States Patent
Buriak

(10) Patent No.: US 6,358,613 B1
(45) Date of Patent: Mar. 19, 2002

(54) FUNCTIONALIZED POROUS SILICON SURFACES

(75) Inventor: Jillian M. Buriak, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/600,557

(22) PCT Filed: Jan. 22, 1999

(86) PCT No.: PCT/US99/01428

§ 371 Date: Jul. 19, 2000

§ 102(e) Date: Jul. 19, 2000

(87) PCT Pub. No.: WO99/37409

PCT Pub. Date: Jul. 29, 1999

Related U.S. Application Data

(60) Provisional application No. 60/072,216, filed on Jan. 22, 1998.

(51) Int. Cl.[7] .................. B32B 09/04; B32B 03/26; B05D 03/00; B05D 03/04; C12Q 01/68
(52) U.S. Cl. ............... 428/446; 428/428; 428/304.4; 427/2.11; 427/2.13; 250/288; 435/4
(58) Field of Search ............................. 428/446, 428, 428/304.4; 427/2.11, 2.13; 250/288; 435/4

(56) References Cited

U.S. PATENT DOCUMENTS

| | | |
|---|---|---|
| 4,735,906 A | 4/1988 | Bastiaans |
| 4,964,972 A | 10/1990 | Sagiv et al. |
| 5,242,828 A | 9/1993 | Bergstrom et al. |
| 5,620,850 A | 4/1997 | Bamdad et al. |
| 6,248,539 B1 * | 6/2001 | Ghadiri et al. ............... 435/7.1 |
| 6,288,390 B1 * | 9/2001 | Siuzdak et al. ............. 250/288 |

OTHER PUBLICATIONS

Buriak et al., "Lewis Acid Mediated Functionalization of Porous Silicon with Substituted Alkenes and Alkynes", *Journal of the American Chemical Society*, vol. 120, pp. 1339–1340 (Feb. 1998).

Lin et al., "A Porous Silicon–Based Optical Interferometric Biosensor", *Science*, vol. 278, pp. 840–843 (Oct. 31, 1997).

Lee et al., "Light–Induced Reactions of Porous and Single–Crystal Si Surfaces with Carboxylic Acids", *J. Am. Chem. Soc.*, vol. 118, pp. 5375–5382 (1996).

Linford et al., "Alkyl Monolayers on Silicon Prepared from 1–Alkenes and Hydrogen–Terminated Silicon", *J. Am. Chem. Soc.*, vol. 117, pp. 3145–3155 (1995).

Zhang et al., "Surface Modification of Porous Silicon by Aluminum Isopropoxide and Its Impact on Electroluminescence", *J. Electrochem. Soc.*, vol. 143, No. 4, pp. 1390–1394 (Apr. 1996).

Canham, L. T., "Silicon quantum wire array fabrication by electrochemical and chemical dissolution of wafers", *Appl. Phys. Lett.*vol. 57, pp. 1046–1048 (Sep. 3, 1990).

Asao et al., "Lewis Acid–Catalyzed trans–hydrosilylation of Alkynes", *J. Org. Chem.*, vol. 67, pp. 7654–7655 (1996).

Oertle et al., "Hydrosilylation of Tetrasubstituted Olefins", *Tetrahedron Letters*, vol. 26, No. 45, pp. 5511–5514 (1985).

* cited by examiner

Primary Examiner—Robert Dawson
Assistant Examiner—Michael J Feely
(74) *Attorney, Agent, or Firm*—Barnes & Thornburg

(57) ABSTRACT

Methods for forming a covalently bound monolayer on silicon surfaces comprising contacting a silicon substrate with an alkene or alkyne in the presence of a solvent-soluble Lewis acid, and porous silicon substrates having surfaces comprising covalently bound monolayers are provided.

18 Claims, 3 Drawing Sheets

FUNCTIONALIZED POROUS SILICON SURFACES

CROSS-REFERENCE TO RELATED APPLICATIONS

This application is a U.S. national application of international application Ser. No. PCT/US99/01428 filed Jan. 22, 1999, which claims priority to U.S. provisional application Ser. No. 60/072,216 filed Jan. 22, 1998.

FIELD OF THE INVENTION

This invention relates to surface functionalized porous silicon substrates. More particularly, this invention is directed to porous silicon surfaces having covalently bound monolayers formed using optionally substituted alkenes and alkynes under exceptionally mild conditions using a solvent-soluble Lewis acid.

BACKGROUND AND SUMMARY OF THE INVENTION

Silicon surface chemistry is of fundamental technical significance because of the ubiquitous role of silicon in modern technology, and yet it is only just beginning to be investigated. Most microprocessor chips in electronic products are based upon crystalline silicon wafers. Control of silicon surface chemistry is crucial to allow access to technologically interesting thin films for fabrication of new electronic devices. In 1990, Canham and co-workers showed that silicon wafers could be etched to produce a microns-thick porous layer (termed porous silicon) that exhibits photoluminescence upon exposure to UV light [Canham, L. T. *Appl. Phys. Lett.* 1990, 57, 1046]. Potential applications for porous silicon include uses as chemical sensors, biosensors, optoelectronic devices such as electroluminescent displays, photodetectors, and as a matrix for photo-pumped tunable lasers. As a result, modification and characterization of photoluminescent porous silicon surfaces has become an area of intense interest.

Hydrosilylation of olefins and alkynes has been known to proceed under a wide variety of reaction conditions. Late transition metal catalysts were commonly used in these reactions, however, such catalysts have the potential for activating the weaker Si—Si bonds on the surface (bond strengths: Si—Si=340 kJ/mol, Si—H=393 kJ/mol). Lewis acid catalyzed/mediated hydrosilylation reactions have also been reported. Aluminum chloride, for example, is known to be an effective catalyst for hydrosilylation of both alkynes and alkenes, but that Lewis acid is not soluble in non-polar solvents and, therefore, is not suitable for solid phase chemistry.

This invention provides a mild and general method for covalent modification of the surface of porous silicon through hydrosilylation of readily available alkynes and alkenes mediated by a Lewis acid such as $EtAlCl_2$ that is soluble in non-polar solvents.

Hydrosilylation of alkynes and alkenes catalyzed by $EtAlCl_2$ and other solvent-soluble Lewis acids by surface situated silicon hydride groups on a porous silicon surface smoothly yields vinyl and alkyl groups, respectively, covalently bound to the surface. The present method is tolerant of a variety of functional groups. Thus, for example, nitrile, hydroxy and methyl ester substituted olefins have been used to form covalently bound monolayers on porous silicon surfaces without additional protecting groups. The "solvent soluble" type of Lewis acid used in accordance with this invention plays a dual role—it mediates the hydrosilylation event, and it acts as a reversible protecting group for Lewis basic sites in the unsaturated reactant that can be removed after the reaction by washing with donating solvents.

This invention also provides porous silicon substrates having a surface comprising a covalently bound monolayer. Such porous silicon substrates are remarkably stable under a wide variety of conditions normally resulting in degradation of the delicate porous surface structure.

DETAILED DESCRIPTION

Figure 1:
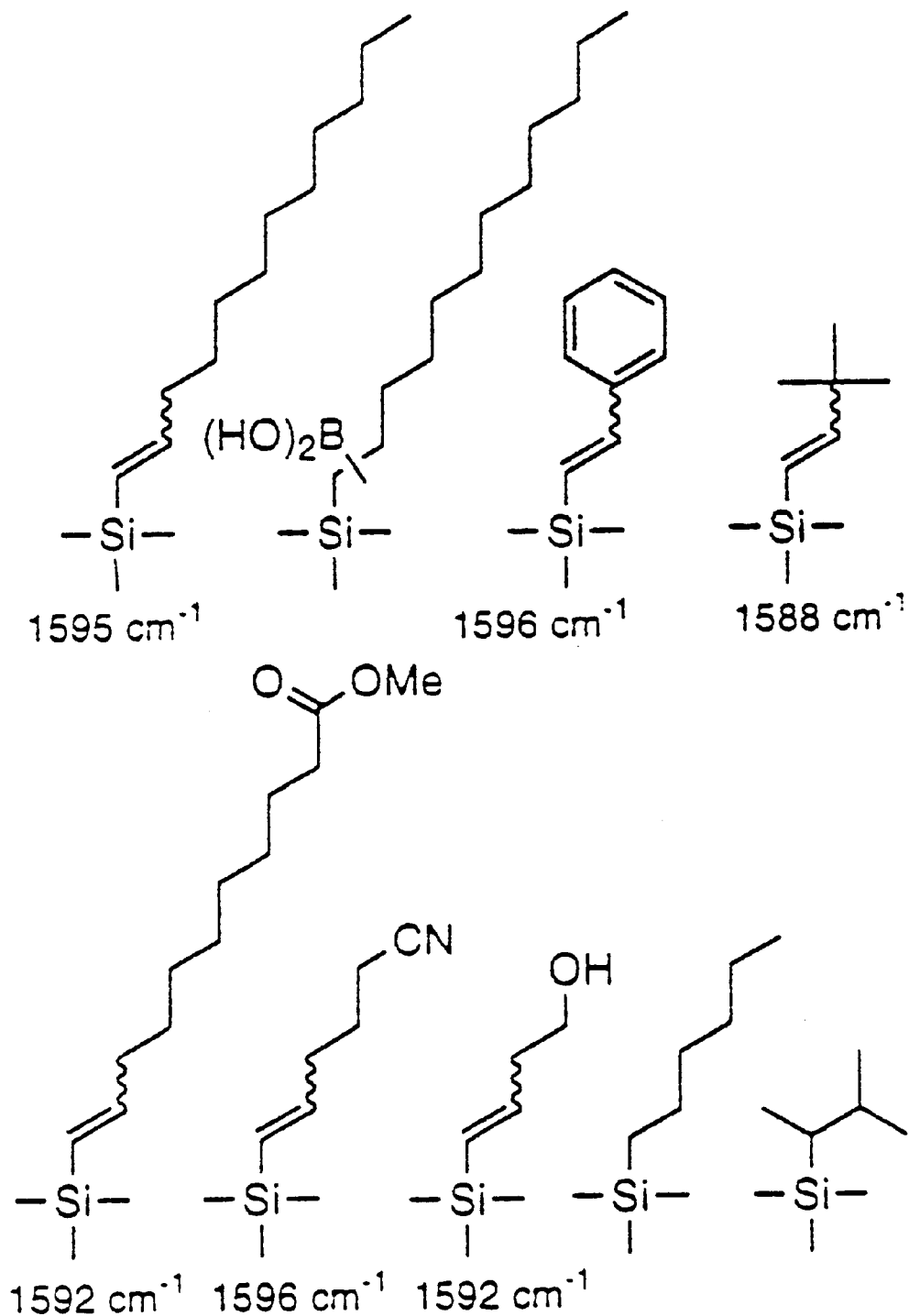
FIG. 1 depicts functional groups covalently bound to the surface of porous silicon through $EtAlCl_2$ mediated hydrosilylation of alkynes and alkenes. The numeric values correspond to the $\upsilon$ (C=C) of the surface-bound vinyl group as measured by transmission FTIR.
Figure 2:
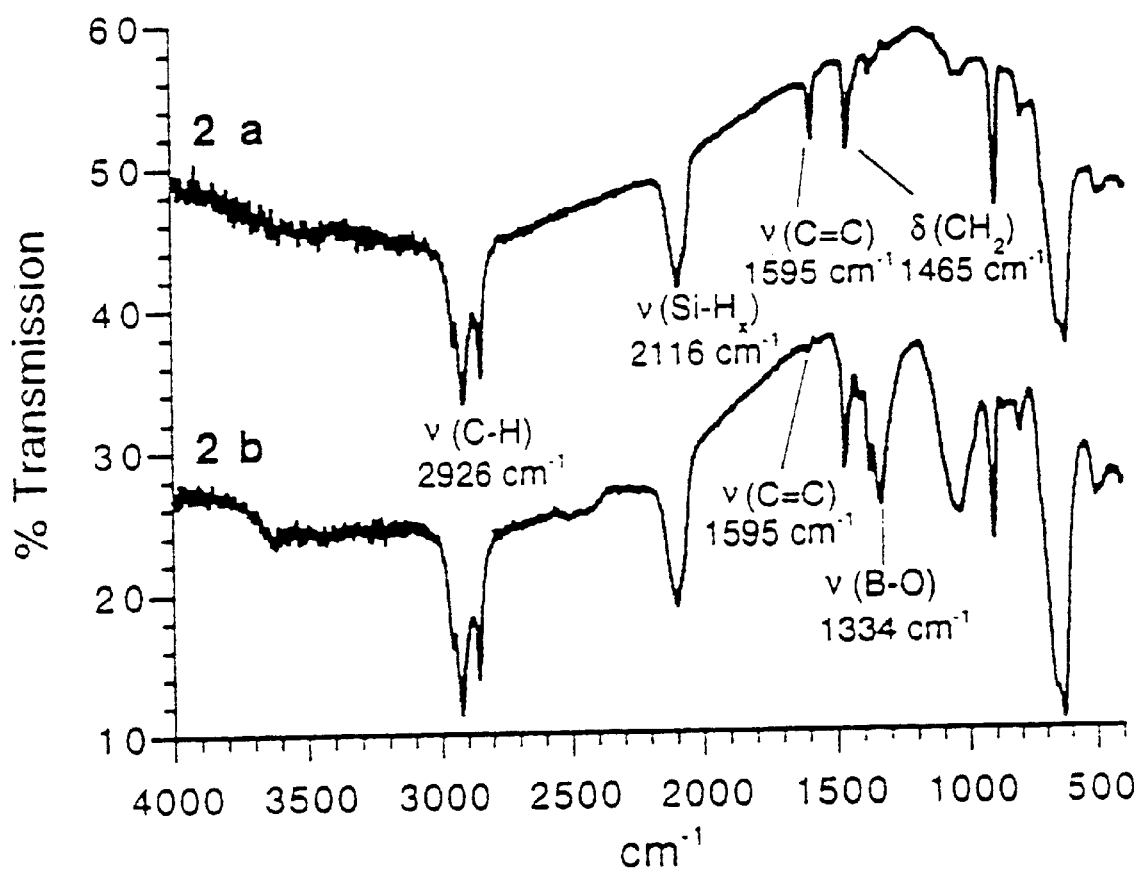
FIG. 2 is an FTIR (transmission mode) of monolayers prepared through: a) hydrosilylation of 1-dodecyne mediated by $EtAlCl_2$ on porous silicon resulting in covalent attachment of a dodecenyl group and b) hydroboration of the olefin of the dodecenyl group with 0.8 M $BH_3THF$ at room temperature for 16 hours.
Figure 3:
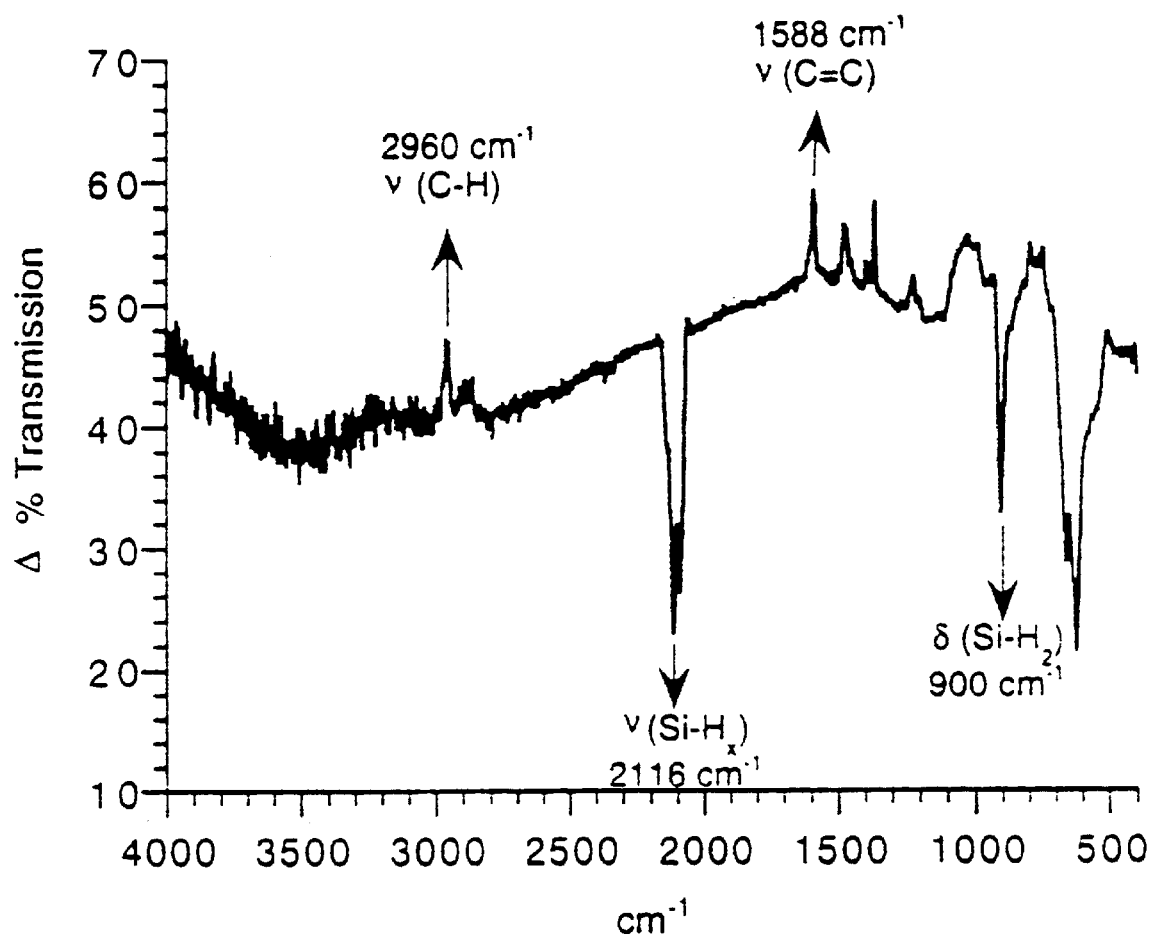
FIG. 3 is a difference spectrum (FTIR, transmission mode) of the monolayer formed through $EtAlCl_2$ mediated hydrosilylation of t-butylacetylene on the porous silicon surface. Silicon hydrides are clearly consumed in the reaction.

In one embodiment, this invention provides a method for forming a covalently bound monolayer on a solid silicon substrate having a surface comprising silicon hydride groups, said method comprising the step of contacting the solid silicon substrate with an amount of an optionally substituted $C_2$–$C_{24}$ alkene or alkyne sufficient to form the monolayer on the surface of the silicon substrate, in the presence of a solvent-soluble Lewis acid. Particularly useful solid silicon substrates are porous silicon and the flat crystalline silicon surface of any crystal face.

In one aspect of this method, the $C_2$–$C_{24}$-alkene or alkyne is a compound of the formula:

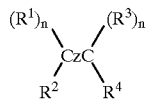

wherein z represents a double or triple bond;

when z is a triple bond, n is 0;

when z is a double bond, n is 1; and $R^1$, $R^2$, $R^3$, and $R^4$ independently, are hydrogen, hydroxy, halo, cyano, isocyano, $C_1$–$C_{18}$ alkoxy, $C_1$–$C_{18}$ carboxy, $C_1$–$C_{18}$ alkoxycarbonyl, primary, secondary or tertiary amino, thiol, optionally substituted phosphino, $BH_2$ or $B(OH)_2$, or $C_1$–$C_{18}$ alkylthio or an optionally substituted $C_1$–$C_{18}$ alkyl, aryl, heteroaryl or vinyl group; and when $R^1$, $R^2$, $R^3$ or $R^4$ is a substituted group, the group is substituted with one or more substituents selected from the group consisting of hydroxy, halo, cyano, aryl, heteroaryl aryl, heteroaryl isocyano, $C_1$–$C_{18}$ alkoxy, $C_1$–$C_{18}$ carboxy, $C_1$–$C_{18}$ alkoxycarbonyl, primary, secondary or tertiary amino, thiol, optionally substituted phosphino, BH, or B(OH)$_2$, or C$_1$–C$_{18}$ alkylthio, halo C$_1$–C$_{18}$ alkyl, cyano C$_1$–C$_{18}$ alkyl, isocyano-C$_1$–C$_{18}$ alkyl, C$_1$–C$_{18}$ carbamido, or C$_1$–C$_{18}$ alkylthio group, a C$_1$–C$_{18}$ ferrocene substituent or another electron donor, a metal chelating ligand or a metal complex thereof, or a biologically significant ligand selected from an antibody, a receptor protein, DNA or RNA, or a DNA or RNA analog capable of forming a double or triple stranded complex with DNA or RNA; or R$^2$ and R$^4$, together with the carbon atoms to which they are attached, form a 5-, 6-, 7- or 8-membered ring.

In accordance with another embodiment, the C$_2$–C$_{24}$-alkene or alkyne is a compound of the formula:

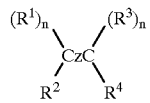

wherein
  z represents a double or triple bond;
  when z is a triple bond, n is 0;
  when z is a double bond, n is 1; and R$^1$ and R$^3$ independently, are hydrogen or C$_1$–C$_4$ alkyl, or R$^1$ and R$^3$ together with the carbon atoms to which they are attached, form a 5-, 6-, 7- or 8-membered ring;
  R$^2$ and R$^4$ independently, are hydrogen or optionally substituted C$_1$–C$_{18}$ alkyl, aryl or heteroaryl, and when R$^2$ or R$^4$ is a substituted group, the group is substituted with one or more substituents from the group consisting of hydroxy, halo, cyano, aryl, heteroaryl, C$_1$–C$_{18}$ alkoxy, carboxy, phospho, phosphino, C$_1$–C$_{18}$ alkoxycarbonyl, primary, secondary or tertiary amino, carbamido, thiol, or C$_1$–C$_{18}$ alkylthio, or R$^2$ and R$^4$, together with the carbon atoms to which they are attached, form a 5-,6-, 7- or 8-membered ring.

In accordance with still another embodiment of the present method, the C$_2$–C$_{24}$-alkene or alkyne is a compound of the formula:

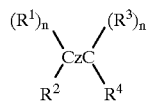

wherein
  z represents a double or triple bond;
  when z is a triple bond, n is 0;
  when z is a double bond, n is 1; and R$^1$ and R$^3$ independently, are hydrogen or C$_1$–C$_4$ alkyl, or R$^1$ and R$^3$ together with the carbon atoms to which they are attached, form a 5-, 6-, 7- or 8-membered ring;
  R$^2$ and R$^4$ independently are hydrogen, aryl, heteroaryl or substituted C$_1$–C$_{18}$ alkyl wherein the substituents are selected from the group consisting of aryl or heteroaryl, and when z is a double bond, R$^1$ and R$^3$ are both hydrogen.

In another preferred embodiment of the present method the R$^2$or R$^4$ group is substituted C$_1$–C$_{18}$ alkyl wherein the substituents are selected from the group consisting of hydroxy, carboxy, amino or thiol, said method further comprising the step of covalently coupling a metal chelating ligand or a biologically significant ligand, ligand, ferrocene or another electron donor, or a biologically significant ligand selected from an antibody, a receptor protein, DNA or RNA, or a DNA or RNA analog capable of forming a double or triple stranded complex with DNA or RNA, to the silicon substrate through the substituent group. The covalent coupling can be accomplished by art-recognized techniques wherein the ligand component is prepared in an activated form (e.g., an active ester or anhydride) capable of reacting with the substituent hydroxy, carboxy, amine or thio group.

In another embodiment, this invention provides porous silicon substrates having a surface comprising a covalently bound monolayer. Porous silicon provides a high surface area, and therefore is uniquely suited for use in sensor construction and electrometric sensing of analytes in test solutions. Porous silicon, however, has been known to be unstable to a wide variety of conditions. The mild reaction conditions associated with the use of solvent-soluble Lewis acids in accordance with the method of this invention provides a stable porous silicon surface.

Thus, one advantage of this invention is that it allows formation of a surface-protecting monolayer under relatively mild conditions, i.e., at room temperature. The invention also provides a method whereby the surface of the porous silicon can be both protected and selectively functionalized with moieties or functional groups that can interact, for example, in some electrometrically detectable manner with predetermined analytes in a test fluid. In another embodiment, the methods and compositions of this invention thus provide for the manufacture of improved biosensors having a biological component that reacts with an analyte in a test solution.

Moreover, porous silicon having a monolayer of covalently bound hydrophobic groups demonstrates remarkable stability. For example, when porous silicon functionalized with hydrophobic groups using this method is subjected to boiling in aerated aqueous KOH (pH 10), no oxidation was seen and only minor changes in the surface IR spectra were noted. When unfunctionalized porous silicon is subjected to those same conditions, the porous layer dissolves. Because of the high stability displayed by porous silicon surfaces protected in accordance with this invention, this methodology represents an important step towards the use of porous silicon in technologically important applications.

This invention further provides a porous silicon substrate or a flat crystalline surface of a crystal face having a surface comprising a covalently bound monolayer wherein the monolayer comprises a substituted or unsubstituted vinyl group of the formula:

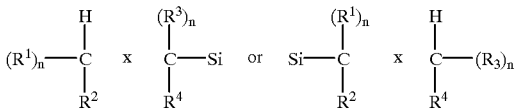

wherein
  Si is a surface silicon atom through which the substituted or unsubstituted vinyl or alkyl group is bonded to the silicon surface;
  x represents a single or double bond;
  when x is a double bond, n is 0;
  when x is a single bond, n is 1;
  R$^1$, R$^2$, R$^3$, and R$^4$ independently, are hydrogen, hydroxy, halo, cyano, isocyano, C$_1$–C$_{18}$ alkoxy, C$_1$–C$_{18}$ carboxy, C$_1$–C$_{18}$ alkoxycarbonyl, primary, secondary or tertiary amino, thiol, optionally substituted phosphino, phospho, BH$_2$ or B(OH)$_2$, or C$_1$–C$_{18}$ alkylthio or an optionally substituted C$_1$–C$_{18}$ alkyl, aryl, heteroaryl or vinyl group; and when $R^1$, $R^2$, $R^3$ or $R^4$ is a substituted group, the group is substituted with one or more substituents selected from the group consisting of hydroxy, halo, cyano, aryl, heteroaryl, isocyano, $C_1$–$C_{18}$ alkoxy, $C_1$–$C_{18}$ carboxy, $C_1$–$C_{18}$ alkoxycarbonyl, primary, secondary or tertiary amino, thiol, optionally substituted phosphino, $BH_2$ or $B(OH)_2$, or $C_1$–$C_{18}$ alkylthio, halo $C_1$–$C_{18}$ alkyl cyano $C_1$–$C_{18}$ alkyl, isocyano-$C_1$–$C_{18}$ alkyl, $C_1$–$C_{18}$ carbamido, or $C_1$–$C_{18}$ alkylthio group, ferrocene or another electron donor, a metal chelating ligand or metal complex thereof, or a biologically significant ligand selected from an antibody, a receptor protein, DNA or RNA, or a DNA or RNA analog capable of forming a double or triple stranded complex with DNA or RNA; or $R^2$ and $R^4$, together with the carbon atoms to which they are attached, form a 5-, 6-, 7- or 8-membered ring.

In accordance with another preferred embodiment a porous silicon substrate or a flat surface of a crystal face having a surface comprising a covalently bound monolayer is provided, wherein the monolayer comprises a substituted or unsubstituted vinyl or alkyl group of the formula:

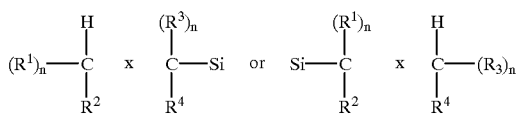

wherein

Si is a surface silicon atom through which the substituted or unsubstituted vinyl or alkyl group is bonded to the silicon surface;

x represents a single or double bond;

when x is a double bond, n is 0;

when x is a single bond, n is 1; and $R^1$ and $R^3$ independently, are hydrogen or $C_1$–$C_4$ alkyl or $R^1$ and $R^3$, together with the carbon atoms to which they are attached, form a 5-, 6-, 7- or 8-membered ring, or $R^1$ is hydrogen and $R^3$ is $BH_2$ or $B(OH)_2$, or $R^1$ is $BH_2$ or $B(OH)_2$, and $R^3$ is hydrogen;

$R^2$ and $R^4$ independently, are hydrogen or optionally substituted $C_1$–$C_{18}$ alkyl, aryl or heteroaryl, and when $R^2$ or $R^4$ is a substituted group, the group is substituted with one or more substituents from the group consisting of hydroxy, halo, cyano, aryl, heteroaryl, $C_1$–$C_{18}$ alkoxy, carboxy, phospho, phosphino, $C_1$–$C_{18}$ alkoxycarbonyl, primary, secondary or tertiary amino, carbamido, thiol, or $C_1$–$C_{18}$ alkylthio, ferrocene or another electron donor, a metal chelating ligand or a metal complex thereof, or a biologically significant ligand selected from an antibody, a receptor protein, DNA or RNA, or a DNA or RNA analog capable of forming a double or triple stranded complex with DNA or RNA; or $R^2$ and $R^4$, together with the carbon atoms to which they are attached, form a 5-, 6-, 7- or 8-membered ring.

In another embodiment of the silicon substrate of this invention $R^1$ and $R^3$ are independently hydrogen, or $C_1$–$C_{18}$ alkyl and $R^2$ and $R^4$ independently, are hydrogen or optionally substituted alkyl, aryl or heteroaryl. In still another embodiment, x is a double bond and $R^2$ or $R^4$ is an optionally substituted aryl or heteroaryl or at least a portion of the $R^2$ or $R^4$ group comprises a biologically significant ligand.

One preferred embodiment of this invention is directed to porous silicon surfaces or flat crystalline surfaces having a surface comprising a covalently bound monolayer comprising a substituted vinyl group of the formula:

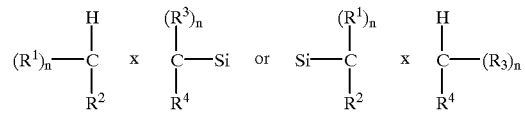

wherein x is a double bond, and one of $R^1$ or $R^4$ comprises a metal chelating ligand and/or a metal complex thereof.

Other preferred aspects of this invention are those porous silicon surfaces or flat crystalline surfaces wherein at least a portion of the covalently bound substituted alkyl or alkenyl groups comprise a biologically significant ligand.

The term "Lewis acid" is understood in the art to be a substance that can accept an electron pair from a base. Lewis acids containing aluminum, boron, tin, hafnium, zirconium, titanium, scandium, yttrium or a lanthanide or actinide can be used in this invention. Lewis acids comprising aluminum are preferred. Preferred acids comprising aluminum are alkylaluminum halides, particularly ethylaluminum dichloride and ethylaluminum sesquichloride, and most particularly ethylaluminum dichloride.

The term "solvent soluble" Lewis acid refers to a Lewis acid that is soluble in a non-polar aprotic solvent. Non-polar aprotic solvents are well known in the art. Examples of useful solvents include hexane, toluene, benzene, cyclohexane, pentane and ligroin. The use of solvent-soluble Lewis acids avoids multiphasic reactions on the surface of porous silicon.

The terms "$C_1$–$C_x$-alkyl" refer to a straight, branched or cyclic alkyl group having the designated (x) number of carbon atoms. It is understood that, if the group is cyclic, it must have a minimum of three carbon atoms.

The term "primary amino" represents an $H_2N$— group. The term "secondary amino" represents an $R^5HN$— group and the term "tertiary amino" represents an $R^5R^6N$— group wherein $R^5$ and $R^6$, independently, represent a hydrogen, $C_1$–$C_6$ alkyl or aryl.

The term "phosphino" refers to a group of the formula $R^5R^6P$— wherein $R^5$ and $R^6$ are as defined supra.

The term "metal chelating ligand" refers to organic groups capable of forming complexes with one or more metal cations, typically metal cations of valence +2, +3, +4 or +5. The term includes art-recognized salt forming groups or groups which form coordinate covalent metal complexes including certain heteroaryl moieties The terms "aryl" and "heteroaryl" are used as they are understood in the art and include both substituted and substituted groups. Examples of useful aryl groups are benzyl and naphthyl. Heteroaryl groups are those aryl groups including mono and bicyclic or polycyclic vinyl groups having one or more hetero-ring atoms. These groups wherein at least one heteroatom is nitrogen are particularly preferred. Examples of such groups include pyridyl, pyrrolyl, bipyridyl phenanthrolyl, pyrazinyl and indolyl.

The term "DNA or RNA analog" refers to a chemical analog of DNA or RNA having other than a phosphate linked sugar "backbone" that is capable of forming a double stranded complex with DNA or RNA.

The alkynes and alkenes react with surface bound Si—H groups to yield surface bound vinyl and alkyl groups, respectively, as outlined in equations 1 and 2.

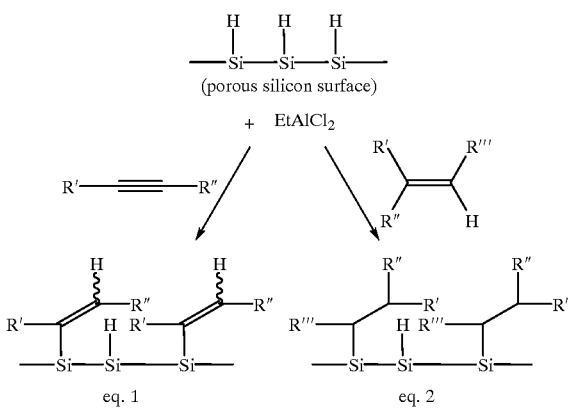

eq. 1        eq. 2

The method of this invention is tolerant of a wide variety of functional groups, as demonstrated through the formation of nitrile, hydroxy and ester terminated surfaces. Porous silicon functionalized with hydrophobic groups using this technique is remarkably stable to adverse conditions, such as boiling aerated water and boiling aqueous KOH (pH 10).

The method of this invention can also be carried out with mixtures of alkynes and alkenes to provide covalently bound surfaces wherein the mole fraction of the groups in the monolayer correspond generally to the mole fractions of the alkynes and/or olefins in the reagent mixture used to form the monolayer.

The method of this invention can also be carried out with mixtures of alkynes and alkenes to provide covalently bound surfaces wherein the mole fraction of the groups in the monolayer correspond generally to the mole fractions of the alkynes and/or olefins in the reagent mixture used to form the monolayer.

Alternatively, covalently bound monolayers comprising mixtures of covalently bound species can be formed by sequentially reacting the surface with less than stoichiometric amounts of alkene or alkyne reactants. Functional groups present on the covalently bound monolayer, e.g., hydroxy, amino, carboxy and thiol, can be used to functionalize the surface further by coupling to biologically significant molecules using standard ester or amide-forming coupling techniques.

In order to illustrate the operation of this invention, the following non-limiting examples are provided:

EXAMPLE 1

Addition of 10 µl of a commercial 1.0 M hexanes solution of $EtAlCl_2$ (10 µmol) to a 0.28 cm² area of porous silicon (galvanostatically etched, n type, P-doped, (100) orientation, 0.83 ohm·cm resistivity Si wafer, 75 mA/cm² current density with illumination by a 300 W tungsten filament bulb, 1:1 solution of EtOH/49% aqueous HF) followed by 3 µl of 1-dodecyne (14 µmol) under nitrogen resulted in clean incorporation of dodecenyl groups on the surface in 1 h at room temperature as shown by transmission FTIR. The resulting disubstituted carbon-carbon double bond appears at 1595 cm$^{-1}$. Although neither the stereochemistry nor ratio of possible regioisomers of surface-bound olefins was determined, molecular hydrosilylation of alkynes catalyzed by $EtAlCl_2$ yields exclusively cis alkenes with perfect regioselectivity when the alkyne is terminal (100% anti-Markovnikov addition). The C=C stretching frequency of the surface bound dodecenyl group correlates well with that reported for the related molecular compound, (Z)-1-triethylsilyl-1-dodecene (1605 cm$^{-1}$), also produced through hydrosilylation of 1-dodecyne with triethylsilane catalyzed by $EtAlCl_2$. Other pertinent features observed by FTIR include the υ (C—H) stretches of the decyl chain between 2960–2850 cm$^{-1}$ and δ (C—H) methylene and methyl bending modes at 1466 and 1387 cm$^{-1}$.

Hydrophobic alkynes incorporated onto the surface in a similar manner include phenylacetylene and the bulky t-butylacetylene. In all cases, the υ (Si—H) centered around 2100 cm$^{-1}$ diminished in intensity, indicating that Si—H groups were consumed in the hydrosilylation reaction. Preferential disappearance of one type of silicon hydride group over another was not noted, as has been observed in other reactions on porous silicon. The reaction did not proceed in the absence of $EtAlCl_2$.

In order to clearly demonstrate that the stretch observed at 1595 cm$^{-1}$ is indeed an olefinic stretch, the dodecenyl terminated surface was hydroborated with excess 0.8 M $BH_3$ THF in THF under nitrogen followed by quenching of the surface in air and rinsing with excess THF. This reaction is illustrated in Equation 3:

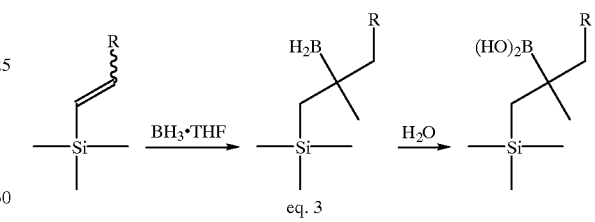

eq. 3

As observed by transmission FTIR, almost quantitative disappearance of the stretch at 1595 cm$^{-1}$ was observed with concomitant appearance of a new stretch at 1334 cm$^{-1}$ which corresponds to the B—O stretching frequency. Cross-linked B—O groups may also be present because of their high local concentration. The stereochemistry of the borane addition was not determined, although the boron atom should add preferentially to the least hindered carbon, that being the carbon β to the surface silyl group.

By using an excess of $EtAlCl_2$, alkynes with coordinating functional groups can be incorporated onto the surface. It was previously noted that, if more than one molar equivalent of Lewis acid was added, alkyne substrates containing silyloxy and benzyloxy groups could be hydrosilylated with triethylsilane. One equivalent of the Lewis acid complexes the coordinating group and the remainder mediates the hydrosilylation reaction.

As a general procedure, 0.2 µl of alkyne (in these examples, this amounts to less than 3 µmol) were added to a 0.28 cm² porous silicon surface previously treated with 10 µl of 1.0 M $EtAlCl_2$ in hexanes (10 µmol) and allowed to react 2 h. In these tests, hydrosilylation of 3-butyn-1-ol, 5-cyano-1-pentyne and methyl 10-undecynoate was carried out smoothly, resulting in hydroxy, nitrile and methyl ester terminated surfaces, respectively. If more than one equivalent of 5-cyano-1-pentyne or methyl 10-undecynoate was added with respect to $EtAlCl_2$, hydrosilylation did not occur because of quantitative coordination of the Lewis acid to either the nitrile or methyl ester. Since $EtAlCl_2$ coordinates to any Lewis basic sites in the unsaturated substrate, it acts as a temporary protecting group, preventing any side reactions. It was noted for 5-cyano-1-pentyne that, if trace oxygen was present, extensive oxidation of the porous silicon surface occurred in the absence of $EtAlCl_2$, apparently induced by the nitrile group. In the presence of excess EtAlCl$_2$, however, hydrosilylation proceeded with no accompanying oxidation. Excess EtAlCl$_2$ could be removed easily at the end of the reaction by rinsing with dry THF, EtOH and CH$_2$Cl$_2$.

Alkene hydrosilylation was carried out on the surface of porous silicon to yield an alkyl terminated surface. For example, 1-hexene and the hindered trisubstituted olefin 2-methyl-2-butene each reacted with a porous silicon surface retreated with 10 μl of 1.0 M hexanes solution of EtAlCl$_2$ to yield the corresponding alkyl substituted surface. Because olefins are less active than alkynes, a greater volume of substrate must be used (100 μl), and the reaction should be allowed to proceed longer (16 h).

The regioselectivity of Si—H addition to the alkene was not determined, but for molecular hydrosilylation of trisubstituted olefins, quantitative anti-Markovnikov addition is observed. Control experiments indicated that hydrosilylation did not proceed in the absence of EtAlCl$_2$.

NMR analysis confirms that hydrosilyation of alkenes and alkynes on hydrogen terminated surfaces can be mediated by a solvent-soluble Lewis acid in accordance with the present invention.

The product formed by synthesis of a soluble model compound through hydrosilylation of 1-dodecyne with triethylsilane as mediated by EtAlCl$_2$ was subjected to $^{13}$C solution phase NMR spectrum (121 MHz). The carbons of the vinyl group were clearly seen at 146 and 120 ppm, with the carbon bound directly to the silicon resonating at the lower frequency. An apparent triplet feature observed to centered around 72 ppm was due to the CDCl$_3$ solvent. Hydrosilylation of 1-dodecyne on hydrogen terminated porous silicon, mediated by EtAlCl$_2$, yields an almost identical spectrum to the model compound [cross-polarized (CP)$^{13}$C solid state NMR spectrum (121 MHz)]. This result provides direct evidence of a vinyl group bound directly to the silicon surface. The two vinyl carbons were seen at 152 and 125 ppm.

The product formed by synthesis of a soluble model compound through hydrosilylation of phenylacetylene with triethylsilane as mediated by EtAlCl$_2$ was analyzed by $^{13}$C solution phase NMR spectrum (121 MHz). The carbons of the vinyl group were clearly seen at 143 and 130 ppm, with the carbon bound directly to the silicon resonating at the lower frequency. An apparent triplet feature observed to centered around 72 ppm was due to the CDCl$_3$ solvent. The other peaks observed at ~127 ppm and 140 ppm are associated with the aromatic ring. Hydrosilylation of phenylacetylene, mediated by EtAlCl$_2$, on hydrogen terminated porous silicon yields an almost identical spectrum to the model compound [cross-polarized (CP)$^{13}$C solid state NMR spectrum (121 MHz)]. This result provides direct evidence of a vinyl group bound directly to the silicon surface. The two vinyl carbons can be seen at 150 and 138 ppm.

The product formed by hydrosilylation of 1-pentyne, mediated by EtAlCl$_2$, on hydrogen terminated porous silicon was analyzed by cross-polarized (CP)$^{13}$C solid state NMR spectrum (121 MHz). The two vinyl carbons were observed at 152 and 125 ppm. The surface was then reduced through a hydroboration reaction with BH$_3$ in order to prove chemically the presence of the vinyl group. As indicated by cross-polarized (CP)$^{13}$C solid state NMR spectrum (121 MHz), the two peaks associated with the presumed vinyl group disappear, clearly proving the olefinic nature of this group.

The hydrophobic alkyl and alkenyl terminated porous silicon surfaces prepared in accordance with the present invention are very stable under highly demanding conditions. For example, the alkyl substituted surfaces formed from hydrosilylation of 1-hexene and 2-methyl-2-butene were both stable to rinsing with a 1:1 solution of EtOH/49% HF (aq) and to boiling 2 h in aerated water (no change in IR spectra). Unmodified porous silicon undergoes substantial oxidation and degradation after 1 h in water at 100° C. More remarkable, the surface formed from hydrosilylation of t-butylacetylene withstood boiling in aerated basic solutions (pH 10) of aqueous KOH and solutions of 25% EtOH/75% aqueous KOH (pH 10) for 1 h with only minor changes in its FTIR spectrum. Unsubstituted porous silicon dissolves rapidly under these conditions.

While surface coverage appears by IR to be incomplete for both alkynes or alkenes, as evidenced by the remaining silicon-hydride groups left on the porous silicon, the stability of these hydrophobic surfaces suggests that exposed areas of the porous silicon are effectively capped. The remaining unreacted silicon-hydride groups must be sterically inaccessible, even to water and hydroxide ion.

This simple, one-step reaction allows access to porous silicon surfaces terminated with a variety of functional groups. Furthermore, incorporation of bulky aliphatic substituents provide highly stable porous silicon surfaces.

What is claimed is:

1. A silicon substrate having a surface comprising a covalently bound monolayer, said monolayer comprising a substituted or unsubstituted vinyl or alkyl group of the formula:

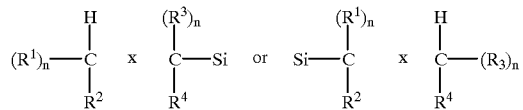

wherein

Si is a surface silicon atom through which the substituted or unsubstituted vinyl or alkyl group is bonded to the silicon surface;

x represents a single or double bond;

when x is a double bond, n is 0;

when x is a single bond, n is 1; and

R$^1$ and R$^3$ independently, are hydrogen or C$_1$–C$_4$ alkyl or R$^1$ and R$^3$, together with the carbon atoms to which they are attached, form a 5-, 6-, 7- or 8-membered ring, or R$^1$ is hydrogen and R$^3$ is BH$_2$ or B(OH)$_2$, or R$^1$ is BH$_2$ or B(OH)$_2$, and R$^3$ is hydrogen;

R$^2$ and R$^4$ independently, are hydrogen or optionally substituted C$_1$–C$_{18}$ alkyl, aryl or heteroaryl, and when R$^2$ or R$^4$ is a substituted group, the group is substituted with one or more substituents from the group consisting of hydroxy, halo, cyano, aryl, heteroaryl, C$_1$–C$_{18}$ alkoxy, carboxy, phospho, phosphino, C$_1$–C$_{18}$ alkoxycarbonyl, primary, secondary or tertiary amino, carbamido, thiol, or C$_1$–C$_{18}$ alkylthio, ferrocene or another electron donor, a metal chelating ligand or a metal complex thereof, or a biologically significant ligand selected from an antibody, a receptor protein, DNA or RNA, or a DNA or RNA analog capable of forming a double or triple stranded complex with DNA or RNA; or R$^2$ and R$^4$, together with the carbon atoms to which they are attached, form a 5-, 6-, 7- or 8-membered ring.

2. The silicon substrate of claim 1 wherein the silicon substrate comprises porous silicon.

3. The silicon substrate of claim 1 wherein the silicon substrate comprises a flat surface of any crystal silicon face.

4. The silicon substrate of claim 1 wherein x is a double bond, and $R^2$, or $R^4$ is a metal chelating ligand, a metal complex thereof, or a biologically significant ligand.

5. The silicon substrate of claim 4 wherein at least a portion of the covalently bound $R^2$ or $R^4$ groups comprise a biologically significant ligand.

6. The silicon substrate of claim 5 wherein $R^2$ is H or $C_1$–$C_4$ alkyl.

7. The Silicon Substrate of claim 1 wherein $R^1$ and $R^3$ are independently hydrogen or $C_1$–$C_4$ alkyl, and $R^2$ and $R^4$ independently, are hydrogen or alkyl, aryl or heteroaryl.

8. The Silicon Substrate of claim 1 wherein x is a double bond and $R^2$ or $R^4$ is an $C_1$–$C_{18}$ alkyl wherein the substituent is aryl, heteroaryl, a metal chelating ligand or metal complex thereof, or a biologically significant ligand.

9. The Silicon Substrate of claim 1 wherein x is a double bond, and one of $R^2$ or $R^4$ is an aryl, heteroaryl, $C_1$–$C_{18}$ alkyl substituted with aryl, heteroaryl or a metal chelating ligand or a metal complex thereof.

10. A method for forming a covalently bound monolayer on a silicon substrate having a surface comprising silicon hydride groups, said method comprising the step of contacting the silicon substrate with an amount of an optionally substituted $C_2$–$C_{24}$ alkene or alkyne sufficient to form the monolayer on the surface of the silicon substrate, in the presence of a solvent-soluble Lewis acid.

11. The method of claim 10 wherein the silicon substrate is porous silicon or a flat surface of any crystal silicon face.

12. The method of claim 11 wherein the alkene or alkyne is a compound of the formula:

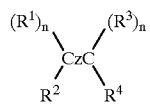

wherein
z represents a double or triple bond;
when z is a triple bond, n is 0;
when z is a double bond, n is 1; and $R^1$ and $R^3$ independently, are hydrogen or $C_1$–$C_4$ alkyl, or $R^1$ and $R^3$ together with the carbon atoms to which they are attached, form a 5-, 6-, 7- or 8-membered ring:
$R^2$ and $R^4$ independently, are hydrogen or optionally substituted $C_1$–$C_{18}$ alkyl, aryl or heteroaryl, and when $R^2$ or $R^4$ is a substituted group, the group is substituted with one or more substituents from the group consisting of hydroxy, halo, cyano, aryl, heteroaryl, $C_1$–$C_{18}$ alkoxy, carboxy, phospho, phosphino, $C_1$–$C_{18}$ alkoxycarbonyl, primary, secondary or tertiary amino, carbamido, thiol, or $C_1$–$C_{18}$ alkylthio, or $R^2$ and $R^4$, together with the carbon atoms to which they are attached, form a 5-,6-, 7- or 8-membered ring.

13. The method of claim 12 wherein the Lewis acid is a solvent-soluble compound of aluminum, boron, tin, hafnium, zirconium, titanium, scandium, yttrium, or a lanthanide or actinide.

14. The method of claim 13 wherein the Lewis acid is an aluminum compound.

15. The method of claim 14 wherein the compound is ethylaluminum dichloride.

16. The method of claim 12 wherein $R^2$ and $R^4$ independently are hydrogen, aryl, heteroaryl or substituted $C_1$–$C_{18}$ alkyl wherein the substituents are selected from the group consisting of aryl or heteroaryl, and when z is a double bond, $R^1$ and $R^3$ are both hydrogen.

17. The method of claim 12 wherein the $R^2$ or $R^4$ group is substituted $C_1$–$C_{18}$ alkyl wherein the substituents are selected from the group consisting of hydroxy, carboxy, amino or thiol, said method further comprising the step of covalently coupling a metal chelating ligand or a biologically significant ligand, ferrocene or another electron donor, or a biologically significant ligand selected from an antibody, a receptor protein, DNA or RNA, or a DNA or RNA analog capable of forming a double or triple stranded complex with DNA or RNA to the silicon substrate through the substituent group.

18. A method for forming a covalently bound monolayer on a silicon substrate having a surface comprising silicon hydride groups, said method comprising the step of contacting the silicon substrate with an amount of an optionally substituted $C_2$–$C_{24}$ alkene or alkyne sufficient to form the monolayer on the surface of the silicon substrate, in the presence of a solvent-soluble Lewis acid, said alkene or alkyne having the formula:

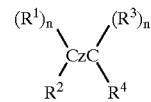

wherein
z represents a double or triple bond;
when z is a triple bond, n is 0;
when z is a double bond, n is 1; and $R^1$ and $R^3$ independently, are hydrogen or $C_1$–$C_4$ alkyl, or $R^1$ and $R^3$ together with the carbon atoms to which they are attached, form a 5-, 6-, 7- or 8-membered ring;
$R^2$ and $R^4$ independently, are hydrogen or optionally substituted $C_1$–$C_{18}$ alkyl, aryl or heteroaryl, and when $R^2$ or $R^4$ is a substituted alkyl group, the group is substituted with one or more substituents from the group consisting of hydroxy, halo, cyano, aryl, heteroaryl, $C_1$–$C_{18}$ alkoxy, carboxy, phospho, phosphino, $C_1$–$C_{18}$ alkoxycarbonyl, primary, secondary or tertiary amino, carbamido, thiol, or $C_1$–$C_{18}$ alkylthio, or $R^2$ and $R^4$, together with the carbon atoms to which they are attached, form a 5-, 6-, 7- or 8-membered ring.

* * * * *